(12) United States Patent
Simola et al.

(10) Patent No.: US 9,977,764 B2
(45) Date of Patent: May 22, 2018

(54) METHOD FOR DESIGNING COIL SYSTEMS FOR GENERATION OF MAGNETIC FIELDS OF DESIRED GEOMETRY, A MAGNETIC RESONANCE IMAGING OR MAGNETOENCEPHALOGRAPHY APPARATUS WITH A COIL ASSEMBLY AND A COMPUTER PROGRAM

(75) Inventors: Juha Simola, Helsinki (FI); Samu Taulu, Helsinki (FI)

(73) Assignee: Elekta AB (publ)., Stockholm (SE)

( * ) Notice: Subject to any disclaimer, the term of this patent is extended or adjusted under 35 U.S.C. 154(b) by 593 days.

(21) Appl. No.: 13/637,650

(22) PCT Filed: Mar. 24, 2011

(86) PCT No.: PCT/FI2011/050249
§ 371 (c)(1),
(2), (4) Date: Sep. 26, 2012

(87) PCT Pub. No.: WO2011/117471
PCT Pub. Date: Sep. 29, 2011

(65) Prior Publication Data
US 2013/0197838 A1    Aug. 1, 2013

(30) Foreign Application Priority Data
Mar. 26, 2010 (FI) ...................................... 20105313

(51) Int. Cl.
*G01R 33/385* (2006.01)
*G01R 33/38* (2006.01)
(Continued)

(52) U.S. Cl.
CPC ............ *G06F 17/12* (2013.01); *A61B 5/0035* (2013.01); *A61B 5/04008* (2013.01);
(Continued)

(58) Field of Classification Search
CPC .. G01R 33/3875; G01R 33/025; G01R 33/34; G01R 33/421; G01R 33/385;
(Continued)

(56) References Cited

U.S. PATENT DOCUMENTS 5,289,151 A * 2/1994 Turner ........................ 335/299
5,594,849 A * 1/1997 Kuc et al. ..................... 345/632
(Continued)

FOREIGN PATENT DOCUMENTS

EP      0 803 737 A2    10/1997
EP      0 933 645 A2     8/1999
(Continued)

OTHER PUBLICATIONS

Michael A. Ohliger and Daniel K. Sodickson, "An introduction to coil array design for parallel MRI," Mar. 2006, John Wiley & Sons, Ltd., NMR Biomed. 19, pp. 300-315.*
(Continued)

*Primary Examiner* — Mischita Henson
*Assistant Examiner* — Christine Liao
(74) *Attorney, Agent, or Firm* — Studebaker & Brackett PC

(57) ABSTRACT

The present invention introduces a method, apparatus and computer program for magnetic resonance imaging or magnetoencephalography applications in order to control currents of a coil assembly (20), and thus achieving desired magnetic fields precisely in the measuring volume (21). The approach is an algebraic method where a field vector is generated for the test currents of each coil (20). Vector and matrix algebra is applied and a linear set of equations is formed. Field components and their derivatives up to the desired order can be taken into account. Principal component analysis or independent component analysis can be applied for determination of the dominant external interfer-
(Continued)

ence components. By checking the condition value for the matrix (33, 45), it is possible to investigate whether a reasonable solution of currents for desired magnetic fields is possible to achieve. Finally, solved currents can be installed into a current supply unit (29) feeding the coils of the assembly (20). The invention can be applied as an active compensation feature for different interference shapes in the MEG application (25), or for the precise creation of the fields and gradients in the MRI application (24).

19 Claims, 4 Drawing Sheets

(51) Int. Cl.

| | | |
|---|---|---|
| *G06F 17/12* | (2006.01) | |
| *A61B 5/04* | (2006.01) | |
| *A61B 5/055* | (2006.01) | |
| *G01R 33/025* | (2006.01) | |
| *G01R 33/381* | (2006.01) | |
| *G01R 33/28* | (2006.01) | |
| *A61B 5/00* | (2006.01) | |
| *G01R 33/421* | (2006.01) | |
| *G01R 33/48* | (2006.01) | |
| *G01R 33/3875* | (2006.01) | |

(52) U.S. Cl.
CPC ............ *A61B 5/055* (2013.01); *G01R 33/025* (2013.01); *G01R 33/28* (2013.01); *G01R 33/381* (2013.01); *G01R 33/385* (2013.01); *G01R 33/3875* (2013.01); *G01R 33/4215* (2013.01); *G01R 33/4808* (2013.01)

(58) Field of Classification Search
CPC .. G01R 33/20; G01R 33/0005; G01R 33/022; G01R 33/482; G01R 33/4822; G01R 33/4833; G01R 33/4215
See application file for complete search history.

(56) References Cited

U.S. PATENT DOCUMENTS

| | | | |
|---|---|---|---|
| 5,661,401 A | 8/1997 | Ishikawa et al. | |
| 5,689,189 A * | 11/1997 | Morich et al. | 324/318 |
| 2006/0244449 A1 * | 11/2006 | Muftuler | G01R 33/3415 324/318 |
| 2008/0294386 A1 * | 11/2008 | Taulu et al. | 702/191 |
| 2008/0312523 A1 * | 12/2008 | Dunseath | 600/383 |
| 2009/0184709 A1 | 7/2009 | Kajola et al. | |
| 2011/0137589 A1 * | 6/2011 | Leskowitz et al. | 702/57 |

FOREIGN PATENT DOCUMENTS

| | | |
|---|---|---|
| EP | 1 612 576 A1 | 1/2006 |
| GB | 2 407 388 A | 4/2005 |
| JP | 2000-037362 A | 2/2000 |
| WO | 02/45582 A1 | 6/2002 |
| WO | 2005/078467 A1 | 8/2005 |
| WO | 2006/114473 A1 | 11/2006 |

OTHER PUBLICATIONS

H. Siebold, "Design Optimization of Main, Gradient, and RF Field Coils for MR Imaging," Mar. 1990, IEEE Transactions on Magnetics, vol. 26, No. 2, pp. 841-846.*
William H. Hayt, Jr. and John A. Buck; "Engineering Electromagnetics"; 2001, McGraw-Hill Higher Education; 6th ed; pp. 224-225.*
Francoise Romeo et al.; Magnet Field Profiling: Analysis and Correcting Coil Design; Magnetic Resonance in Medicine; 1984, vol. 1, Issue 1, pp. 44-65.
R. Turner; A target field approach to optimal coil design; Journal of Physics D; Applied Physics, 1986, vol. 19, No. 8; pp. L147-L151.
Michael Poole et al.; Minimax current density coil design; Journal of Physics D; Applied Physics; 2010, vol. 43, No. 9; published Feb. 15, 2010.
International Search Report dated Jun. 30, 2011; International Application No. PCT/FI2011/050249.
Search Report issued by National Board of Patents and Registration of Finland dated Nov. 17, 2010 Application No. 20105313.
Vadim S. Zotev et al.; "Microtesla MRI of the human brain combined with MEG"; Journal of Magnetic Resonance; 2008; pp. 115-120; vol. 194.
The extended European search report issued by the European Patent Office on Jun. 28, 2016, which corresponds to European Patent Application No. 11758880.6-1568 and is related to U.S. Appl. No. 13/637,650.
Robert Turner et al.; "Gradient Coil Design: A Review of Methods"; Magnetic Resonance Imaging; Jan. 1, 1993; pp. 903-920; vol. 11; No. 7; Elsevier Science; Tarrytown, NY, US.
Patrick N. Morgan et al.; "Resistive Homogeneous MRI Magnet Design by Matrix Subset Selection"; Magnetic Resonance in Medicine; Jan. 1, 1999; pp. 1221-1229, vol. 41; John Wiley & Sons, Inc.; US.

* cited by examiner

METHOD FOR DESIGNING COIL SYSTEMS FOR GENERATION OF MAGNETIC FIELDS OF DESIRED GEOMETRY, A MAGNETIC RESONANCE IMAGING OR MAGNETOENCEPHALOGRAPHY APPARATUS WITH A COIL ASSEMBLY AND A COMPUTER PROGRAM

FIELD OF THE INVENTION

The invention relates to magnetic imaging technologies and specifically to creation of magnetic fields of specified, geometrically precise shape over a large volume in space.

BACKGROUND OF THE INVENTION

Magnetic fields of precise geometry are needed in medical magnetic imaging applications, like magnetic resonance imaging (MRI) and magnetoencephalography (MEG). Recently, also combination of the two imaging techniques has been proposed ("Microtesla MRI on the human brain combined with MEG", Vadim S. Zotev et al, Journ. Mag. Res. 194, pp 115-120, 2008).

In the MRI method the part of the human body that is studied is exposed to a uniform magnetic field, and to gradients of the field for decoding of the spatial information contained in the MRI signal. The geometry of the measuring field essentially contributes to the signal quality and geometric precision of the resulting MRI image. An ideal measuring field is free of field derivatives higher than first.

In the MEG method the very weak magnetic signals resulting from the functioning of the human brain are recorded by sensors located around the head. One of the main problems in this technique is the protection of the measuring device against the environmental magnetic interference the strength of which may exceed the signals of interest by seven to eight orders of magnitude. This magnetic shielding problem can be solved by active compensation methods that counteract the interference using coil systems tailored to produce counter fields that very precisely match the geometry of the interference fields (see patent application PCT/FI2005/000090).

The interference fields in a typical MEG recording environment are relatively uniform and smooth. "Smooth" means here that the fields comprise of spatially uniform field components and only low order spatial derivatives of these components. Spatial derivatives higher than first order, say, are of very small amplitude in the interference. This is so because these fields arise from sources tens of meters away from the recording device, and are additionally smoothed by the magnetically shielding room (MSR) housing the MEG device. Therefore, the fields used to counteract these interference fields in an active compensation arrangement must also be smooth and tailored to optimally match the interference field geometry. This enables maximal compensation of the interference over relatively large volume of the size of the human head.

In both MRI and MEG methods the coil systems must be located relatively close to the measuring device. This way the currents needed to create the measuring and counteracting fields stay reasonably small. Furthermore, if a feedback principle is used for the active compensation the compensation coils must necessarily be inside the MSR (PCT/FI2005/000090). Placing the coils outside of the MSR would cause extra delay and lead to unstable feedback loop.

The requirements that the fields must be uniform or smooth over a large measuring volume, and must be generated by coils located near this volume, at a distance of one to two meters only, are contradictory. Field profiles generated by close-by coils necessarily contain second and higher derivatives, and the coils must be carefully designed to produce smooth fields and gradients over a volume as large as the size of human head, for example.

A well-known, elementary example toward the solution of this kind of coil design problem are the so called Helmholz and Maxwell pairs: By properly choosing the distance between two circular, coaxial coils of same size one can create, mid between the two coils, an axial field $B_x$ uniform up to the fourth derivative $dB_x/dx$ is $d^4B_x/dx^4$. The coil assembly optimized this way is called a Helmholz-pair. The first non-zero derivative of its field is $d^4B_x/dx^4$. A spatially constant axial derivative $dB_x/dx$ smooth up to fifth derivative is created by a coil set called a Maxwell-pair where the first non-zero odd derivative beyond $dB_x/dx$ is $d^5B_x/dx^5$. But, to generate uniform magnetic fields in all three spatial directions ($B_x$, $B_y$, $B_z$), and their derivatives—constant over a macroscopic volume—one must design a coil assembly that simultaneously controls the magnetic fields in the three orthogonal directions, the five independent first derivatives of these components, and the seven independent second derivatives etc. This requirement formulates a kind of "generalized Helmholz/Maxwell coil design problem". Obviously, to solve this problem, a larger number of independent coils is needed than the two coils in the Helmholz and Maxwell cases.

For practical applications this coil design problem is further complicated by the presence of magnetic materials in the vicinity of the coils, and specifically in MEG, by the presence of the MSR. Its walls contain material of high magnetic susceptibility which gets magnetized in the field produced by the current in the coils. This results in a considerable scattered field that is added to the direct field of the coils. The susceptibility values of the MSR wall elements and the characteristics of the joints between the elements vary from one MSR to another and may even change with time. Therefore designing the coil assembly by a mere calculation would require measurement and characterization of the room structure and magnetic properties of the wall elements in such a detailed manner that it is practically impossible.

OBJECTIVE OF THE INVENTION

The objective of this invention is to present a method by which one can design a coil assembly that is able to produce uniform and smooth magnetic fields up to any desired order, even in the case that the immediate environment of the coil assembly contains magnetic materials.

SUMMARY OF THE INVENTION

In the present invention the magnetic field geometry is controlled by properly selecting the $n_c$ currents, current vector I, fed into the $n_c$ coils of a geometrically fixed coil assembly. Each coil in the assembly is characterized by the field components and their gradients that it generates at a given point in space (origin). The key point of the invention is that by including in this characterization a "field-vector" $B_c$ for each coil and also field shapes (derivatives) which are wanted to be excluded from the generated fields, it is possible to formulate a simple algebraic method for calculating the current vectors I needed to 1) give the desired field components or derivatives of them and 2) keep those derivatives at zero which are wanted to be vanished at the origin.

The field-vectors $B_c$ needed for the characterization of each coil can be calculated or measured. The latter approach is necessary in an environment containing magnetic materials.

Described in more explicit manner, the present invention introduces a method of designing coil assemblies for creation of magnetic fields that have desired geometric shapes around a given origin. The method is characterized in that it comprises the following steps:

decomposing a field, created around the origin by a test current in each coil at a time, into desired and undesired components of the field, forming a system of linear equations based on the decomposed components that gives the same decomposition of the field that results from simultaneous powering of the coils of the coil assembly by a set of unknown currents, and determining the set of unknown currents that result in the desired geometric shapes of the fields by solving the system of linear equations.

In an embodiment of the present invention, the decomposition of the field of each coil is calculated around the origin from the geometry of the coil assembly using equations that describe behaviour of the magnetic field in vacuum.

In an embodiment of the present invention, the decomposition of the field of each coil is obtained from a measurement of the magnetic field distribution around the origin caused by the test current in said coil.

In an embodiment of the present invention, the desired field components and the undesired field components are constructed from three orthogonal components of the magnetic field and their independent Cartesian derivatives.

In an embodiment of the present invention, the desired field components are constructed from three orthogonal components of the magnetic field and their five independent Cartesian derivatives of the first order, and the undesired field components are seven independent Cartesian derivatives of the second order.

In an embodiment of the present invention, the unknown current vector is calculated by a product of a Moore-Penrose pseudo-inverse of a matrix comprising the field component vectors for each of the coils with the test current, and the summed field vector of the simultaneous powered coils at the origin.

In an embodiment of the present invention, the method further comprises the following steps:

determining a degree of singularity of the said matrix by a condition number, and in case the condition number of the said matrix exceeds a desired threshold value, thus indicating a singular or substantially singular matrix, modifying the coil assembly, and when the redetermined condition number of the said matrix is below the desired threshold value, thus indicating a non-singular matrix, calculating the set of unknown currents.

In an embodiment of the present invention, the desired field components comprise at least one dominant external interference component, or one or several linear combinations of the dominant external interference components, determined from a separate measurement of interference.

In an embodiment of the present invention, the dominant external interference components used as desired field components are determined from a principal component analysis or an independent component analysis of the separate measurement of interference.

In an embodiment of the present invention, the linear combinations of the dominant external interference components are used as feedback field shapes in an active compensation system, where the linear combinations forming the feedback field shapes, and the locations and orientations of the sensors, are chosen so that the coupling between simultaneously operating feedback loops is minimized.

In an embodiment of the present invention, the method further comprises switching between the magnetic resonance imaging functionality creating the magnetic fields with gradients, and the magnetoencephalography device functionality performing active compensation for the environmental interference.

According to a second aspect of the present invention, the inventive idea also comprises a magnetic resonance imaging or magnetoencephalography apparatus with a coil assembly for creation of magnetic fields that have desired geometric shapes around a given origin, comprising:

a sensor array comprising plurality of sensors for measuring multi-channel data, and control means for controlling the apparatus. The apparatus is characterized in that it further comprises:

the control means configured to decompose a field, created around the origin by a test current in each coil at a time, into desired and undesired components of the field, the control means configured to form a system of linear equations based on the decomposed components that gives the same decomposition of the field that results from simultaneous powering of the coils of the coil assembly by a set of unknown currents, and the control means configured to determine the set of unknown currents that result in the desired geometric shapes of the fields by solving the system of linear equations.

In an embodiment of the present invention, the control means is configured to calculate decomposition of the field of each coil around the origin from the geometry of the coil assembly using equations that describe behaviour of the magnetic field in vacuum.

In an embodiment of the present invention, the control means is configured to obtain the decomposition of the field of each coil from a measurement of the magnetic field distribution around the origin caused by the test current in said coil.

In an embodiment of the present invention, the control means is configured to construct the desired field components and the undesired field components from three orthogonal components of the magnetic field and their independent Cartesian derivatives.

In an embodiment of the present invention, the control means is configured to construct the desired field components from three orthogonal components of the magnetic field and their five independent Cartesian derivatives of the first order, and the undesired field components are seven independent Cartesian derivatives of the second order.

In an embodiment of the present invention, the control means is configured to calculate the unknown current vector by a product of a Moore-Penrose pseudo-inverse of a matrix comprising the field component vectors for each of the coils with the test current, and the summed field vector of the simultaneous powered coils at the origin.

In an embodiment of the present invention, the apparatus further comprises:

the control means configured to determine a degree of singularity of the said matrix by a condition number, and in case the condition number of the said matrix exceeds a desired threshold value, thus indicating a singular or substantially singular matrix, modifying means is configured to modify the coil assembly, and when the predetermined condition number of the said matrix is below the desired threshold value, thus indicating a non-singular matrix, the control means is configured to calculate the set of unknown currents.

In an embodiment of the present invention, the desired field components comprise at least one dominant external interference component, or one or several linear combinations of the dominant external interference components, determined from a separate measurement of interference.

In an embodiment of the present invention, the control means is configured to determine the dominant external interference components used as desired field components from a principal component analysis or an independent component analysis of the separate measurement of interference.

In an embodiment of the present invention, the control means is configured to use the linear combinations of the dominant external interference components as feedback field shapes in an active compensation system, where the linear combinations forming the feedback field shapes, and the locations and orientations of the sensors, are chosen so that the coupling between simultaneously operating feedback loops is minimized.

In an embodiment of the present invention, the apparatus further comprises switching means in order to choose between the magnetic resonance imaging functionality configured to create the magnetic fields with gradients, and the magnetoencephalography device functionality configured to perform active compensation for the environmental interference.

According to a third aspect of the invention, the inventive idea further comprises a computer program for controlling a creation of magnetic fields with a coil assembly which fields have desired geometric shapes around a given origin. The computer program is characterized in that it comprises code adapted to perform the following steps when executed on a data-processing device:

decomposing a field, created around the origin by a test current in each coil at a time, into desired and undesired components of the field, forming a system of linear equations based on the decomposed components that gives the same decomposition of the field that results from simultaneous powering of the coils of the coil assembly by a set of unknown currents, and determining the set of unknown currents that result in the desired geometric shapes of the fields by solving the system of linear equations.

The advantages of the present invention are that with the presented coil assembly design method we can produce desired and accurate magnetic fields with the assembly which is able to effectively compensate different kinds of active interference situations over a relatively large volume. A further advantage is that this design method is mainly implemented with matrix algebra, and therefore the application of the invention can be performed in a straightforward manner in the existing control logic or processor of the MEG device, for instance. A further advantage is that the measuring volume to be compensated is large, and finally, the method is even applicable inside the magnetically shielding rooms which typically include magnetic materials, previously interfering the active compensation systems significantly.

DETAILED DESCRIPTION OF THE INVENTION

Figure 1:
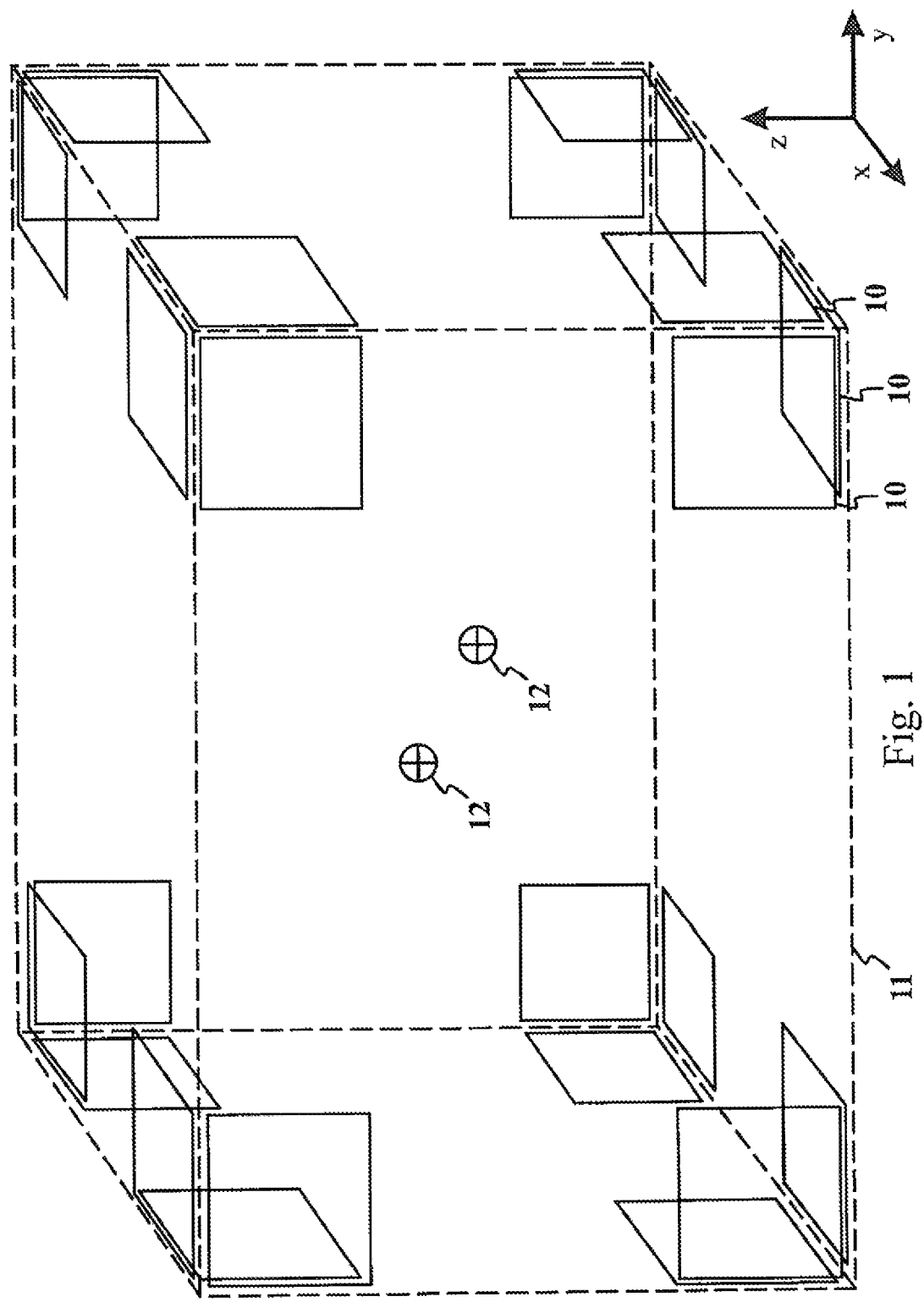
FIG. 1 discloses an example of an assembly of square shaped field generating coils around a measurement volume, FIG. 2 discloses an embodiment of the electronics arrangement controlling the currents in the coil assembly to either provide the measuring field and gradients for the MRI device or the active compensation of the environmental interference of the MEG device, FIG. 3 discloses an embodiment of the method as a flow chart of the process of the coil assembly design for the MRI application, and FIG. 4 discloses an embodiment of the method as a flow chart of the process of the coil assembly design for the active interference cancellation in MEG.

Reference will now be made in detail to the embodiments of the present invention.

The present invention formulates a method for solving the "generalized Helmholz/Maxwell design problem" described in the background section. The method can be extended in a straightforward manner beyond the Helmholz and Maxwell design problems, that is, for designing coil assemblies that create magnetic fields with vanishing derivatives up to any required order. For simplicity, the derivatives are cut to second order in the examples below. However, in a situation where the coils are located close to the measured object and where very smooth and homogenous magnetic fields are desired, we might use derivatives of even higher order than two. The orders of the derivatives taken into the calculations can be chosen according to the accuracy requirements in the used application. Of course, the greater amount of the derivatives taken into account increases the complexity of the calculations (the dimensions of the vectors and matrices), but the main principle of the algebraic operations remain the same.

Three different conditions in which the method can be applied, for instance, are described in the following. The design conditions are presented in the order of increasing complexity.

First we describe the first condition where the method according to the invention can be applied.

In this simplest case the coil assembly is located in an environment that contains no magnetic materials, and the goal is to generate, at a given point inside the coil assembly (the origin), strictly uniform fields in the three Cartesian directions ($B_x$, $B_y$, $B_z$), and constant first derivatives of these three components.

In a volume that is free of magnetic sources (magnetic materials or electric currents) the divergence and curl of magnetic field are zero. Therefore, out of the nine possible first derivatives ($dB_x/dx$, $dB_x/dy$, $dB_x/dz$, $dB_y/dx$, $dB_y/dy$, $dB_y/dz$, $dB_z/dx$, $dB_z/dy$, $dB_z/dz$) only five are independent, for example $dB_x/dx$, $dB_x/dy$, $dB_x/dz$, $dB_y/dy$, and $dB_y/dz$. Similarly, for a divergence and curl free vector field in three dimensional space, out of the 27 second derivatives only seven are independent, for example $d^2B_x/dx^2$, $d^2B_x/dxdy$, $d^2B_x/dxdz$, $d^2B_y/dxdy$, $d^2B_x/dx^2$, $d^2B_y/dy^2$, $d^2B_y/dydz$ and $d^2B_x/dydz$.

A set of $n_c$ coils is specified and the three magnetic field components, the five first derivatives, and the seven second derivatives of the fields arising from the current running in each one of the coils are calculated at the origin. In an environment free of magnetic materials this can be done by using simple, well known mathematical expressions. In this way for each of the $n_c$ coils a field-vector, $B_c$, is obtained with fifteen components, which are $B_x$, $B_y$, $B_z$, $dB_x/dx$, $dB_x/dy$, $dB_x/dz$, $dB_y/dy$, $dB_y/dz$, $d^2B_x/dx^2$, $d^2B/dxdy$, $d^2B_x/dxdz$, $d^2B_y/dxdy$, $d^2B_y/dx^2$, $d^2B_y/dy^2$, $d^2B_y/dydz$, and $d^2B_x/dydz$.

Using these $n_c$ field-vectors as column vectors, a $15 \times n_c$ matrix M is formed. If the $n_c$ coils are simultaneously powered with currents $I_1, I_2, \ldots I_{nc}$, the resulting field vector for the whole assembly, at the origin, is given by the matrix equation $$B = MI \qquad (1)$$

where I is a column vector with components $I_1, I_2, \ldots I_{nc}$, which are the currents in the individual coils. Thus, the current vector needed to create any field vector B is obtained from the equation $$I = \text{inv}(M)B. \qquad (2)$$

Here inv (M) is inverse matrix of M if the number of coils is the same as the number of components in the field vector B, 15 in this example. If the number of coils is smaller or larger than the number of components in the field vector, then inv (M) is the Moore-Penrose pseudo-inverse of M.

For example, the currents needed in the coils of the assembly to create a uniform field of one Tesla in the x-direction, $B_x$, are obtained from equation (2) by using the column vector $B=[1, 0, 0, \ldots 0]$. The field generated by the resulting I-vector is in the x-direction, that is $B_y$, $B_z=0$. In addition, all of its first, and second order derivatives are zero at the origin. It should be noted that the field derivatives up to second order vanish in the origin only because they are included the model ($B_c$-vector) for each coil. Derivatives left out from the $B_c$-vectors are not controlled in the algorithm defined by equations (1) and (2).

The only design problem left after equation (2) is that the overall geometry of the coil assembly must be so chosen that the matrix M is not singular, and thus inv (M) exists. This is not difficult because M is strictly singular only for highly symmetric assemblies. From practical point of view it also matters how close to singular M is. If M is close to singular, creation of some field components or their derivatives may require very high currents in some of the coils. Therefore, the condition number of matrix M, which is a measure of how close to singular M is, is a good measure of the quality of geometric design of the coil assembly also. In case we have a coil assembly located e.g. on a single plane or in otherwise symmetrical mutual locations, it usually occurs that at least one of the resulting currents in the compensating coil assembly needs to be notably high in order to work properly. This is not feasible or economical. Therefore, a good measure for indicating this kind of behaviour is the condition number which in that uneconomical case would be big (e.g. over 100). In order to minimize the condition number, we must relocate the coil assembly e.g. in a less symmetrical fashion, and then we will achieve an optimal coil assembly where with relatively small currents it is possible to accomplish a well-functioning system for creation of smooth measuring field in MRI or effective active compensation in MEG.

The cases where the number of coils in the assembly is 1) equal to, 2) larger than, or 3) smaller than the number of components in the field vector B differ in principle from, each other.

Case 1) is the simplest. Here the number of coils (available "degrees of freedom") is the same as the number of quantities to control (the three field components and their 5+7 independent derivatives at the origin). In this case M is a 15×15 square matrix and equation (2) has a unique solution. The current vector I needed to create a uniform field in the z-direction, $B_z$, for example, is obtained from equation (2) by using the column vector $B=\{0, 0, 1, 0, \ldots, 0\}$. The resulting field is precisely (with numerical accuracy) along the z-axis and all its derivatives up to the second derivatives vanish at the origin.

In case 2) the system defined by equation (1) is underdetermined. The number of coils is larger than the number of quantities to be controlled. In this case equation (1) has an infinite number of solutions I. The solution given by the Moore-Penrose pseudo-inverse is the one that has the smallest Euclidian norm, that is, the smallest length of the vector I. In this case another optimal solution I can also be chosen: the shortest vector I among those solutions that have non-zero currents only in 15 of the $n_c$ coils. This is a way to find out which ones of the $n_c$ coils are least useful for creation of the uniform fields and constant first derivatives, and could possibly be left out from the assembly. This latter solution usually requires higher maximal currents than the Moore-Penrose pseudo-inverse solution.

In the overdetermined case 3) an exact solution I for equation (1) does not exist. Here the number of the available degrees of freedom (number of coils) is smaller than the number of quantities to be controlled. In this case the Moore-Penrose pseudo-inverse gives a vector I that is optimal in the sense that it minimizes the Euclidian norm of the deviation I-MB. This current vector I is a least squares solution to the overdetermined problem.

The number of components in vector B, and in all the $B_c$'s can be increased to include derivative orders higher than two. This may be needed if uniform fields and precise first gradients are needed over a relatively large volume, like in the MRI application. Or this may be needed in the active shielding application if the interference contains components expressing complicated geometry, that is, higher derivatives. To achieve a satisfactory result in this case the number of coils in the assembly must also be increased.

A second condition where the method according to the invention can be applied, is described in the following.

In reality the coil assembly will be installed in a building environment that has magnetic materials and structures. Specifically, in the case of MEG, the magnetically shielding room with its high permeability walls will be quite close to the coils, resulting in a considerable scattered field. The geometry and magnetic properties of these materials are usually complicated and impossible to characterize in detail. Therefore, obtaining the $B_c$ vectors for each coil by calculation may be inaccurate or impossible. In this case, the assembly of coils must be made and installed first, and then the field vectors $B_c$ must be measured one at a time by feeding current into each coil in the assembly. For example, in the case of MEG—and in devices possibly combining MEG and MRI in the same instrument—measuring the field and its derivatives is straightforward because the MEG device itself contains an array of a large number of magnetic sensors. From the response, a signal vector, of the MEG sensor array to the current excitation fed into each one of the coils, the field components and their derivatives needed for $B_c$ are easily derived. If an MEG sensor array is not available, the measurement of the field and its derivatives can be made with some other accurately calibrated sensor array, or with one sensor that can be accurately moved around the origin.

After the $B_c$-vectors for each coil have been determined by measurement, the procedure for obtaining the I-vectors corresponding to the different components of B is applied exactly as in the first condition above.

A third condition where the method according to the invention can be applied, is described in the following.

This third case applies to the MEG application of the present method. The goal in the MRI application is to use the coils to get uniform field components and constant gradients (first derivatives) over the measurement volume, whereas in the MEG application the goal is to be able to counteract the environmental magnetic interference as precisely as possible. This is not necessarily optimally done by cancelling the uniform fields and the spatially constant first derivatives only, because the dominant interference field shapes inside an MSR may contain higher derivatives. Therefore, to achieve optimal cancellation one must determine the current distributions I that accurately reproduce the actual dominant interference field patterns, but exclude the unwanted higher derivative field shapes.

The actual dominant interference patterns can be determined by recording the interference signal with the MEG system (no subject in the helmet) and making for example a principal component analysis (PCA) on the multichannel MEG signal. Another embodiment; is to make an independent component analysis (ICA) on the multichannel MEG signal. After this the present method can be applied so that the first $n_c$ components of the $B_c$-vectors are the projections of the coil signal along the dominant $n_p$ principal components of the previously recorded interference. To prevent the appearance of the unwanted higher derivatives in the cancellation fields, the rest of the components in the $B_c$-vectors are chosen among these higher derivatives.

In principle, in the third condition exactly the same procedure is applied as in the second condition. In the $B_c$-vectors the first few components ($B_x$, $B_y$, $B_z$, . . . ) are only replaced by the dominant PCA components of the actual, measured interference.

In the active compensation application in MEG the interference cancellation runs as a feedback system. Magnetometer sensors on different sides of the MEG helmet are used as zero detectors in feedback loops that control the currents in the compensating coil assembly (PCT/FI2005/000090). Several of such feedback loops run in parallel to compensate for the rip dominant PCA components of the environmental interference. It is advantageous for the stable functioning of such a system of parallel feedback loops to maximally decouple the loops from each other. The coil combination driven by one loop should create a minimal signal in the zero detectors of the other loops. This prevents the counteractions from circulating among the different control loops and therefore makes the entire control system faster and stable over a wider bandwidth.

This orthogonalization of the control system, is built, in the first and second conditions above. This is because in these conditions the controlled field shapes are orthogonal Cartesian components; it is natural to choose the zero detector sensor for the $B_x$-feedback loop strictly in x-direction so that it does not see the $B_y$ and $B_x$ components etc.

This, however, is not automatically the case if the third condition is used to achieve maximal interference compensation. The $n_p$ dominant PCA-components are not "pure" magnetic field components precisely orthogonal in space. Even if the first three of them are nearly uniform fields and define "principal interference directions" in three dimensions, these directions are often rotated with respect to the principal directions of the measuring device and the coil assembly. In this case the parallel feedback loops can be optimally decoupled by mixing the dominant $n_p$ PCA components of the interference with a proper linear transformation within the signal subspace defined by these PCA components. The optimal linear transformation is constructed so that it rotates the coordinate system defined by the PCA components along the principal axes of the device and mixes the interference field shapes so that the zero detector of any feedback loop does not see the counteraction fields related to the other control loops.

To construct the mathematical formalism, let us first denote the $n_{ch} \times n_p$ and $n_{ch} \times n_c$ dimensional PGA and coil signal subspaces by matrices P and C, respectively. Here $n_{ch}$ is the number of measurement channels. Also, let us denote the actual signal vector containing measurement, values from all channels by f. Now, the task is to produce a counteracting signal as precise to f as possible, given the set of coil signals C.

Mathematically, this can be formulated as $$f \approx -CKf_0, \qquad (3)$$

wherein in the simplest case K is an $n_c \times n_c$ dimensional identity matrix so that, the coil signals are used without any kind of mixing, and the $n_c \times 1$ dimensional vector $f_0$ contains feedback information from the zero detectors. However, K may not provide the optimal compensation result as an identity matrix. This can be seen easily by first expressing the signal vector f as a combination of the dominating interference as f=Px and by extracting the contribution of the zero detectors from f and P as $f_0 = P_0 x$, so that $$x = \text{pinv}(P_0) * f_c \qquad (4)$$

Here pinv ($P_0$) denotes pseudo inverse of $P_0$. By setting f=Px and solving for K in such a way that (3) holds true as accurately as possible, we have $$K = \text{pinv}(C) * P * \text{pinv}(P_0) \qquad (5)$$

This is the optimal coil mixing matrix. As a final step, we can remove the cross-talk between the zero detectors by rotating the matrix K. First, set $C_2 = CK$. The rotation $K_{orth} = KR$ will be done so that in the rotated set $C_3 = C_2 R = CKR$ the zero detectors will be orthogonal, i.e., $C_{20} R = I$ is a $n_z \times n_z$ dimensional identity matrix, where $n_z$ is the number of zero detectors and $C_{20}$ only contains the contribution of the zero detectors. Thus, we have R=pinv ($C_{23}$) and the rotated mixing matrix is $$K_{orth} = K * \text{pinv}(C_{20}) \qquad (6)$$

By utilizing an embodiment according to the method of the present invention, one and the same coil assembly can be used for MRI field and gradient generation, and for MEG active cancellation of interference in a combined MEG/MRI instrument. In these cases and in one embodiment of the invention, the MRI electronics controlling magnetic resonance imaging measurement fields can function as a host device. In that case the MEG device can act as a slave device for the MRI electronics, the MEG device being the measuring instrument, for the magnetic resonance signal.

The same coil system can also be used for different measurement locations (origins) within the coil assembly, like seated and supine measurement positions in MEG. The vectors $B_c$ for each coil in the assembly only need to be determined for each measurement location separately, either by calculation or measurement. The same applies to the environmental interference field PCA analysis in the third condition. After this the current distributions I for each of the measurement locations will be obtained from equation (2). Because the $B_c$-vectors and thus the M-matrices are different for the two measurement positions, the resulting I-vectors will also differ. But there is no need to use different coil assemblies, or move or geometrically change the coil assembly when changing from one measurement position to the other. Also, possible repositioning of the measuring device with respect to the coil assembly only requires determination of a new M-matrix, and then calculation of new current vectors I using equation (2).

Reference is now made to the additional examples, which are illustrated in the accompanying drawings.

FIG. 1 shows one possible assembly of square shaped field generating coils around the measurement volume, in an embodiment of the present invention. The twenty-four coils 10 are arranged in groups of three coils in each of the eight corners of a rectangular frame 11. The three coils 10 in each corner are orthogonal to each other. If the measuring device is placed in a magnetically shielding room the frame 11 can be the inside wall of the room. Two possible locations for the origin, centers of the measuring volume, are indicated as 12.

Figure 2:
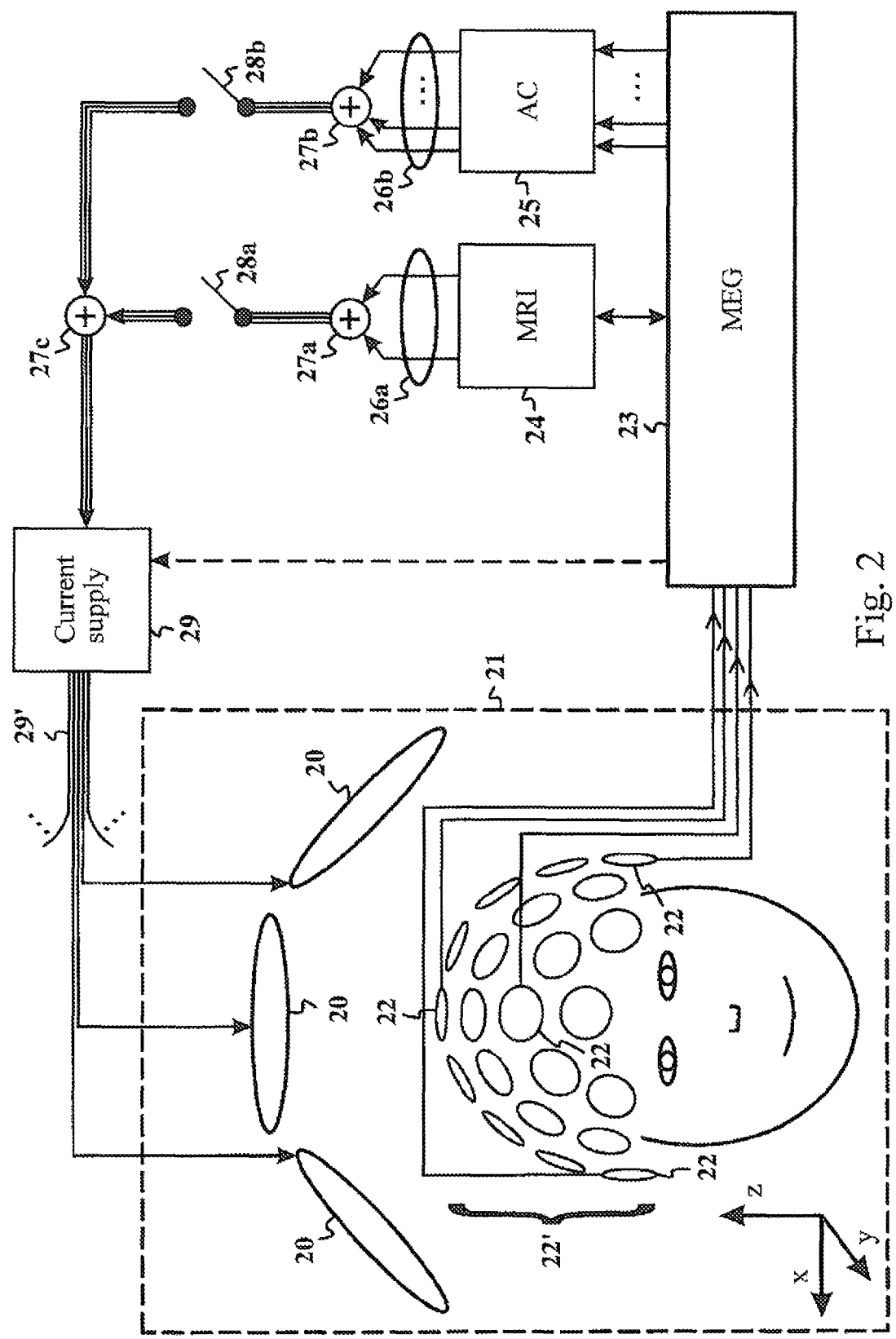

FIG. 2 shows the electronics arrangement controlling the currents in the coil assembly 20 to provide either the measuring field and gradients for an MRI device, or the active compensation of the environmental interference of the MEG device, in an embodiment of the present invention. The measuring volume (e.g. a MSR) is depicted as 21 where the patient is located in the vicinity of the measuring sensors 22. The setting up the system begins with determination of the field vectors $B_c$ for the coils 20 of the assembly in its environment. The data acquisition electronics 23 commands the current supply 29 having $n_c$ outputs 29' to feed current into the coils 20 in the assembly, each one at a time. The resulting coil signals are recorded by the magnetometer channel array 22' and stored in the acquisition system 23.

For setting up the MRI-function 24, these coil signals are decomposed into the Cartesian field components and their derivatives, which are the components of the $B_c$-vectors for the MRI application. After this the M-matrix is formed from these $B_c$-vectors, and the current vectors $I_{MRI}$ are determined by taking the inverse of M. Each one of these $I_{MRI}$-vectors, when fed as input to the current supply 29, will result in a pure Cartesian measuring field or a pure gradient field. These vectors are stored in the MRI control unit 24. In the MRI function this unit controls the timing of the MRI sequence, and the recording field geometries by sending the proper $I_{MRI}$-vectors—of both the uniform field and the gradient—via the link 26a to the $n_c$-channel current supply 29.

If the active interference compensation function is operated following the second condition above then these $I_{MRI}$ current vectors can be used for active compensation as well. But if the third condition is applied, then information from the PCA analysis of the interference must be used for defining the $B_c$-vectors. The recorded coil signals are now decomposed in a coordinate system comprising of the first $n_p$ PCA components of the interference and then higher derivatives of the B-field components (see also FIG. 4). This leads to $B_c$-vectors and M-matrix slightly different from the MRI case, and to current vectors $I_{AC}$ that differ from the vectors $I_{MRI}$. When active compensation 25 is on, the $n_p$ first ones of these $I_{AC}$ vectors are multiplied by the error signals received from the sensors 22 used as zero detectors for the compensation feedback loops, and then transmitted via the link 26b through adders 27b and 27c and switch 28b to the current supply 29. By the two switches 28a-b on the links 26a-b one can choose between the MRI 24 and MEG (active compensation) 25 functions. In the MRI mode, the adder unit 27a adds the two vectors $I_{MRI}$ that correspond to the MRI measuring field and the chosen gradient. Whereas, in the MEG mode during active compensation, the adder unit 27b adds the $I_{AC}$-vectors (weighted by the $n_p$ error signals) to form an $n_c$-component current vector that counteracts the dominant interference components (the $n_p$ PCA components of it). Both these signals are fed to the current supply 29 through the adder unit 27c, with the chosen mode switched on (28a or 28b). In one embodiment, as disclosed earlier regarding the MRI measurements, the MRI electronics 24 can function as a host device to the MEG measurement unit 23 which can be set as a slave device working as measuring instrument for the magnetic resonance signals. This is expressed in FIG. 2 as a two-way arrow between the two units 23, 24.

Figure 3:
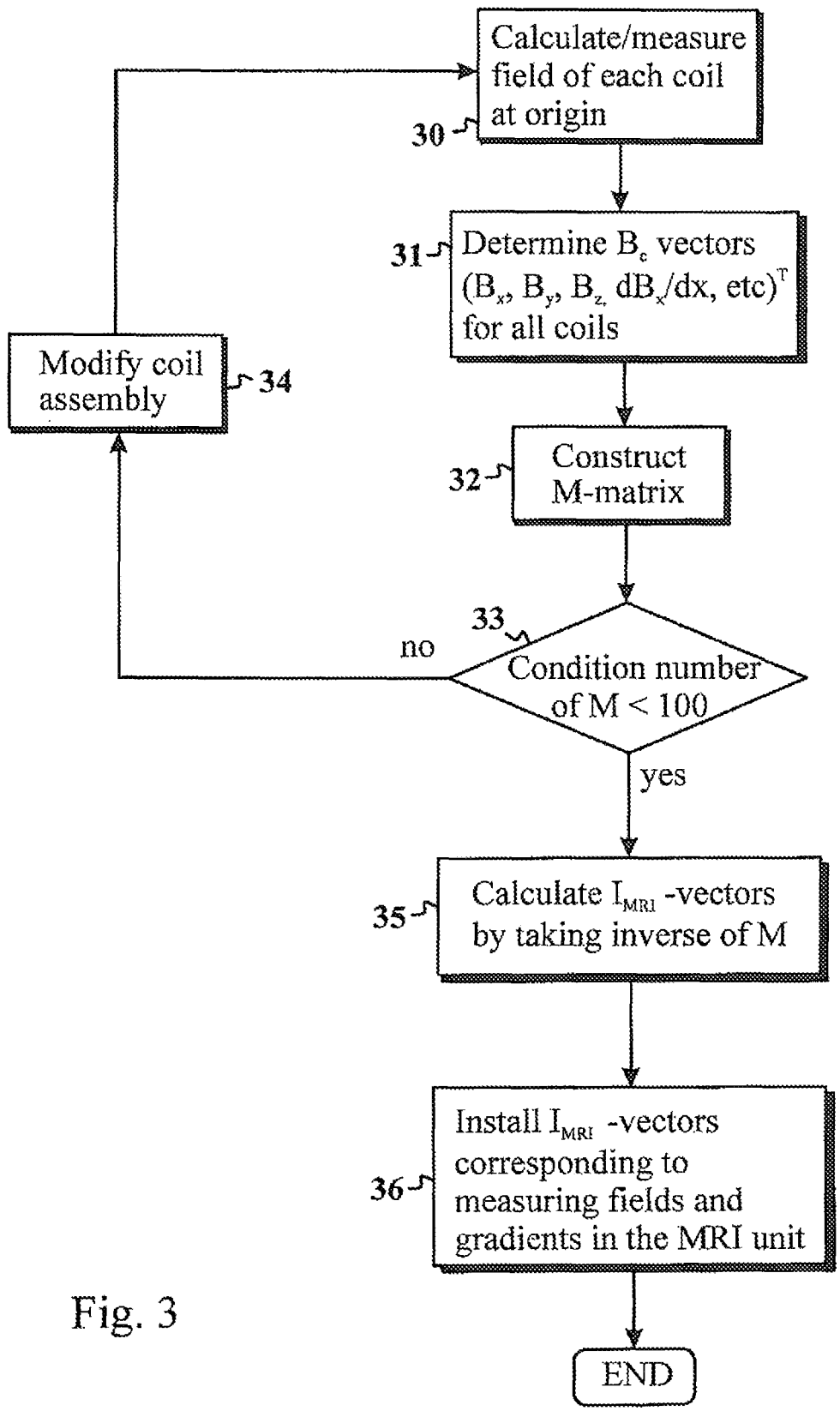

FIG. 3 shows an embodiment of the method according to the invention, as a flow chart of the process of designing coil assembly for the MRI application. This chart is kind of a summary of the steps already handled in the previous paragraphs. In the first step in the procedure, the magnetic field produced by each coil in the assembly is calculated or measured at origin 30. After this we determine a field vector $B_c$ (column vector comprising elements $B_x$, $B_y$, $B_z$, $dB_x/dx$, . . . ) for all the coils in the assembly 31. Then we are ready to construct the matrix M 32 from the field vectors for all coils. After this we can determine the condition number of M 33, which tells how close to singular the matrix M actually is. If the condition number is more than a hundred (or any other desired threshold value), we have to modify the coil assembly 34. Depending on the situation, this means relocating or reorienting the individual coils, or decreasing or increasing the number of coils in the assembly. In that case, we have to start from the beginning of the procedure, and calculate or measure the fields for each coil of the modified assembly again 30.

When we result in the condition number less than a hundred, we may decide that the coil assembly is feasible, and we may calculate 35 the current vectors $I_{MRI}$ according to equation (2). Finally, in the last step 36, we can install the $I_{MRI}$-vectors in the MRI unit which correspond to the measuring fields and gradients.

Figure 4:
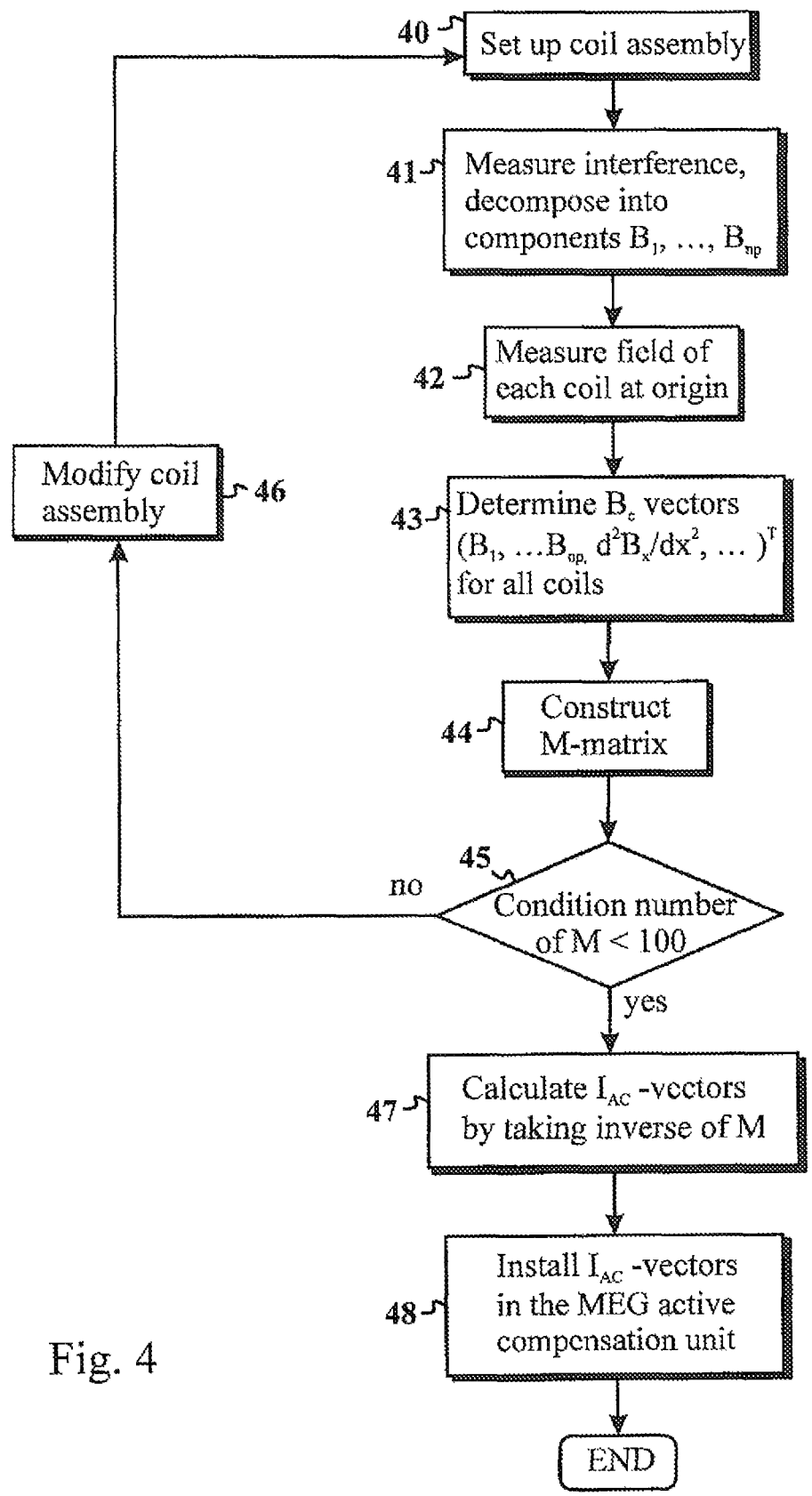

FIG. 4 shows an example as a flow chart of the process of coil assembly design for another application, the active interference cancellation in MEG. At first, we set up the assembly of compensating coils 40 into the measuring volume, e.g. inside a MSR. Then we can measure the background interference 41 without any object present, and decompose this interfering field into components $B_1$, $B_2$, . . . , $B_{np}$ ($n_p$ means the number of dominant PCA components of the interference). After this we may measure the magnetic fields originating from each coil at the origin 42. Then we can determine the field vectors $B_c$ ($B_1$, $B_2$, . . . , $B_{np}$, $d^2B_x/dx^2$, . . . )$^7$ for all the coils 43. When we have the $B_c$'s, we can construct the matrix M 44. Similarly as in the embodiment of FIG. 3, we can check the condition number of the matrix M 45, that is, check whether the matrix M is singular, close to singular or far from singular. We have to modify the assembly of coils 46 and remeasure the background interference until we achieve a matrix M which can be inverted (condition number less than 100, or any other desired threshold value). In that case we can calculate the current vectors $I_{AC}$ 47 by using the equation (2). Finally, we can install the vectors $I_{AC}$ to the active compensation unit of the MEG device 46.

The presented method can be implemented by a computer program which can control a data-processing device to execute the applicable method steps. The computer program can be stored in a medium applicable by the processor or other control means.

It is obvious to a person skilled in the art that with the advancement of technology, the basic idea of the invention may be implemented in various ways. Thus, the invention and its embodiments are not limited to the examples described above; instead, they may vary within the scope of the claims.

The invention claimed is:

1. A method of controlling a magnetic field of a geometrically fixed coil assembly to thereby create magnetic fields of a geometrically precise shape as required in medical magnetic imaging applications around a given origin, the method comprising:

decomposing a field, created around the origin by a test current in each coil of the geometrically fixed coil assembly at a time, into desired and undesired components of the field, wherein the desired components correspond to components giving rise to the geometrically precise shape and the undesired components correspond to other components, forming a system of linear equations based on the decomposed components that gives the same decomposition of the field that results from simultaneous powering of the coils of the geometrically fixed coil assembly by a set of unknown currents, determining the set of unknown currents that result in the geometrically precise shape of the fields by solving the system of linear equations, and applying the set of unknown currents to the coils of the geometrically fixed coil assembly to thereby create magnetic fields that have the geometrically precise shape, wherein the decomposition of the field of each coil is obtained from a measurement of the magnetic field distribution around the origin caused by the test current in said coil, and the desired field components comprise at least one dominant external interference component, or one or several linear combinations of the dominant external interference components, determined from a separate measurement of interference, the linear combinations of the dominant external interference components being used as feedback field shapes in an active compensation system.

2. A method according to claim 1, wherein the decomposition of the field of each coil is calculated around the origin from the geometry of the coil assembly using equations that describe behaviour of the magnetic field in vacuum.

3. A method according to claim 1, wherein the desired field components and the undesired field components are constructed from three orthogonal components of the magnetic field and their independent Cartesian derivatives.

4. A method according to claim 1, wherein the desired field components are constructed from three orthogonal components of the magnetic field and their five independent Cartesian derivatives of the first order, and the undesired field components are seven independent Cartesian derivatives of the second order.

5. A method according to claim 1, wherein the unknown current vector is calculated by a product of a Moore-Penrose pseudo-inverse of a matrix comprising the field component vectors for each of the coils with the test current, and the summed field vector of the simultaneous powered coils at the origin.

6. A method according to claim 5, wherein the method further comprises the following steps:

determining a degree of singularity of the said matrix by a condition number, and in case the condition number of the said matrix exceeds a desired threshold value, thus indicating a singular or substantially singular matrix, modifying the coil assembly, and when the redetermined condition number of the said matrix is below the desired threshold value, thus indicating a non-singular matrix, and calculating the set of unknown currents.

7. A method according to claim 1, wherein the dominant external interference components used as desired field components are determined from a principal component analysis or an independent component analysis of the separate measurement of interference.

8. A method according to claim 1, wherein the linear combinations forming the feedback field shapes, and the locations and orientations of the sensors, are chosen so that the coupling between simultaneously operating feedback loops is minimized.

9. A method according to claim 1, wherein the method further comprises switching between the magnetic resonance imaging functionality creating the magnetic fields with gradients, and the magnetoencephalography device functionality performing active compensation for the environmental interference.

10. A magnetic resonance imaging or magnetoencephalography apparatus with a geometrically fixed coil assembly for controlling a magnetic field of the geometrically fixed coil assembly to thereby create magnetic fields of a geometrically precise shape as required in medical magnetic imaging applications around a given origin, comprising:

a sensor array comprising plurality of sensors for measuring multi-channel data, and control means for controlling the apparatus, wherein:

the control means is configured to decompose a field, created around the origin by a test current in each coil of the geometrically fixed coil assembly at a time, into desired and undesired components of the field, wherein the desired components correspond to components giving rise to the geometrically precise shape and the undesired components correspond to other components, the control means is configured to form a system of linear equations based on the decomposed components that gives the same decomposition of the field that results from simultaneous powering of the coils of the geometrically fixed coil assembly by a set of unknown currents, the control means is configured to determine the set of unknown currents that result in the geometrically precise shape of the fields by solving the system of linear equations, the control means is configured to apply the set of unknown currents to the coils of the geometrically fixed coil assembly to thereby create magnetic fields that have the geometrically precise shape, the control means is configured to obtain the decomposition of the field of each coil from a measurement of the magnetic field distribution around the origin caused by the test current in said coil, and the desired field components comprise at least one dominant external interference component, or one or several linear combinations of the dominant external interference components, determined from a separate measurement of interference, and the control means is configured to use the linear combinations of the dominant external interference components as feedback field shapes in an active compensation system.

11. An apparatus according to claim 10, wherein the control means is configured to calculate decomposition of the field of each coil around the origin from the geometry of the coil assembly using equations that describe behaviour of the magnetic field in vacuum.

12. An apparatus according to claim 10, wherein the control means is configured to construct the desired field components and the undesired field components from three orthogonal components of the magnetic field and their independent Cartesian derivatives.

13. An apparatus according to claim 10, wherein the control means is configured to construct the desired field components from three orthogonal components of the magnetic field and their five independent Cartesian derivatives of the first order, and the undesired field components are seven independent Cartesian derivatives of the second order.

14. An apparatus according to claim 10, wherein the control means is configured to calculate the unknown current vector by a product of a Moore-Penrose pseudo-inverse of a matrix comprising the field component vectors for each of the coils with the test current, and the summed field vector of the simultaneous powered coils at the origin.

15. An apparatus according to claim 14, wherein the apparatus further comprises:
the control means is configured to determine a degree of singularity of the said matrix by a condition number, and in case the condition number of the said matrix exceeds a desired threshold value, thus indicating a singular or substantially singular matrix,
modifying means is configured to modify the coil assembly, and when the redetermined condition number of the said matrix is below the desired threshold value, thus indicating a non-singular matrix, and
the control means is configured to calculate the set of unknown currents.

16. An apparatus according to claim 10, wherein the control means is configured to determine the dominant external interference components used as desired field components from a principal component analysis or an independent component analysis of the separate measurement of interference.

17. An apparatus according to claim 10, wherein the linear combinations forming the feedback field shapes, and the locations and orientations of the sensors, are chosen so that the coupling between simultaneously operating feedback loops is minimized.

18. An apparatus according to claim 10, wherein the apparatus further comprises switching means in order to choose between the magnetic resonance imaging functionality configured to create the magnetic fields with gradients, and the magnetoencephalography device functionality configured to perform active compensation for the environmental interference.

19. A non-transitory computer readable medium containing a computer program for controlling a magnetic field of a geometrically fixed coil assembly to thereby create magnetic fields of a geometrically precise shape as required in medical magnetic imaging applications around a given origin, the computer program comprises code adapted to perform the following steps when executed on a data-processing device:
decomposing a field, created around the origin by a test current in each coil of the geometrically fixed coil assembly at a time, into desired and undesired components of the field, wherein the desired components correspond to components giving rise to the geometrically precise shape and the undesired components correspond to other components,
forming a system of linear equations based on the decomposed components that gives the same decomposition of the field that results from simultaneous powering of the coils of the geometrically fixed coil assembly by a set of unknown currents,
determining the set of unknown currents that result in the geometrically precise shape of the fields by solving the system of linear equations, and
applying the set of unknown currents to the coils of the geometrically fixed coil assembly to thereby create magnetic fields that have the geometrically precise shape,
wherein the decomposition of the field of each coil is obtained from a measurement of the magnetic field distribution around the origin caused by the test current in said coil, and
the desired field components comprise at least one dominant external interference component, or one or several linear combinations of the dominant external interference components, determined from a separate measurement of interference, the linear combinations of the dominant external interference components being used as feedback field shapes in an active compensation system.

* * * * *